(12) United States Patent
Dhindsa

(10) Patent No.: US 6,533,720 B1
(45) Date of Patent: Mar. 18, 2003

(54) MODULAR ENDOSCOPE VALVE ASSEMBLY AND METHOD

(76) Inventor: Avtar S. Dhindsa, 3305 Greyfox Dr., Valparaiso, IN (US) 46383

( * ) Notice: Subject to any disclaimer, the term of this patent is extended or adjusted under 35 U.S.C. 154(b) by 0 days.

(21) Appl. No.: 09/761,784

(22) Filed: Jan. 17, 2001

(51) Int. Cl.$^7$ ................................................. A61B 1/12
(52) U.S. Cl. ..................................... 600/159; 600/105
(58) Field of Search ................................ 600/105, 159, 600/135, 158, 156, 153, 131

(56) References Cited

U.S. PATENT DOCUMENTS

| | | | |
|---|---|---|---|
| 591,228 A | 10/1897 | Gotermann | |
| 1,668,865 A | 5/1928 | Nelson | |
| 2,691,370 A | 10/1954 | Wallace | |
| 3,027,913 A | 4/1962 | Chatham et al. | |
| 3,144,020 A | 8/1964 | Zingale | |
| 3,765,447 A | 10/1973 | Cornell | |
| 3,791,379 A | 2/1974 | Storz | |
| 4,132,227 A | 1/1979 | Ibe | |
| 4,284,101 A | 8/1981 | Weirich | |
| 4,497,468 A | 2/1985 | Hubbard et al. | |
| 4,535,919 A | 8/1985 | Jameson | |
| 4,557,255 A | 12/1985 | Goodman | |
| 4,567,880 A | * 2/1986 | Goodman | 600/135 |
| 4,572,163 A | * 2/1986 | Collins | 251/322 |
| 4,874,066 A | 10/1989 | Silberstein | |
| 4,881,523 A | * 11/1989 | Heckele | 600/131 |
| 5,020,514 A | * 6/1991 | Heckele | 600/107 |
| 5,064,168 A | 11/1991 | Raines et al. | |
| 5,125,910 A | * 6/1992 | Freitas | 600/159 |
| 5,201,908 A | * 4/1993 | Jones | 600/123 |
| 5,207,213 A | 5/1993 | Auhll et al. | |
| 5,228,646 A | 7/1993 | Raines | |
| 5,290,279 A | 3/1994 | Bonati et al. | |
| 5,324,254 A | 6/1994 | Phillips | |
| 5,447,148 A | * 9/1995 | Oneda et al. | 600/131 |
| 5,483,991 A | 1/1996 | D'Agostino et al. | |
| 5,536,234 A | 7/1996 | Newman | |
| 5,647,840 A | 7/1997 | D'Amelio et al. | |
| 5,792,139 A | 8/1998 | Chambers et al | |
| 5,830,126 A | 11/1998 | Odanaka et al. | |
| 5,913,816 A | 6/1999 | Sanders et al. | |
| 5,944,654 A | 8/1999 | Crawford | |
| 5,967,179 A | 10/1999 | Kazakis et al. | |
| 6,383,132 B1 | * 5/2002 | Wimmer | 600/101 |

OTHER PUBLICATIONS

"Pathfinder Plus Continuous and Pulsatile Irrigation Bulb," Utah Medical Products, 1 page, Jan. 5, 1999.

(List continued on next page.)

Primary Examiner—Linda C. M. Dvorak
Assistant Examiner—Jocelyn Ram
(74) Attorney, Agent, or Firm—Brinks Hofer Gilson & Lione

(57) ABSTRACT

A modular endoscope valve assembly is releasably mounted on the handpiece of an endoscope. This valve assembly includes an inlet port, an outlet port, and a valve manually operable selectively to block and to allow the flow of irrigation fluid from the inlet port to the outlet port. The valve assembly is releasably held to the handpiece of the endoscope by a mechanical fastener such as a pressure-sensitive adhesive, a strap, a snap lock, or otherwise. Once the valve assembly is releasably mounted to the handpiece, the physician using the endoscope can manually control the flow of irrigation fluid with the same hand as the one that supports the handpiece, thereby leaving the other hand of the physician free for surgical procedures. The modular valve assembly of this invention can be used with the widest variety of endoscopes, including flexible, rigid and semi rigid ureteroscopes as well as various percutaneous endoscopes.

38 Claims, 3 Drawing Sheets

OTHER PUBLICATIONS

"Utah Medical Products Inc., Pathfinder Plus, An Advancement in Physician Controlled Irrigation, Pathfinder Plus Endoscopic Surgical Irrigators," http://www.utahmed.com/pathfind/htm, 2 pages, Apr. 19, 2000.

"Utah Medical Products Inc., Pathfinder Plus Specifications," http://www.utahmed.com/pathfinds.htm, 1 page, Apr. 19, 2000.

"Now All You Need is the Perfect Valve," B. Braun Medical Inc., 1 page, 2001.

"Distortion–Free Hydro Laparoscopes with Distal Lens Warming," Circon Corporation, p. L–7, (undated).

"Corsion Suction–Irrigation Probes 005200–903," Circon Corporation, 2 pages, 2000.

"Opti4 Laparoscopic Handset and Electrodes," http://www.valleylab.com/displayproduct.cfm?productid=128&menu=product, 1 page, 2002.

Photographs of "Opti4 Laparoscopic Handset and Electrodes" showing interior mechanisms, 2 pages (photos taken May 2002).

"Modular Endoscope Valve Assembly and Method," U.S. Patent Application Ser. No. 10/022,134, filed Dec. 12, 2001; inventor: Avtar S. Dhindsa.

* cited by examiner

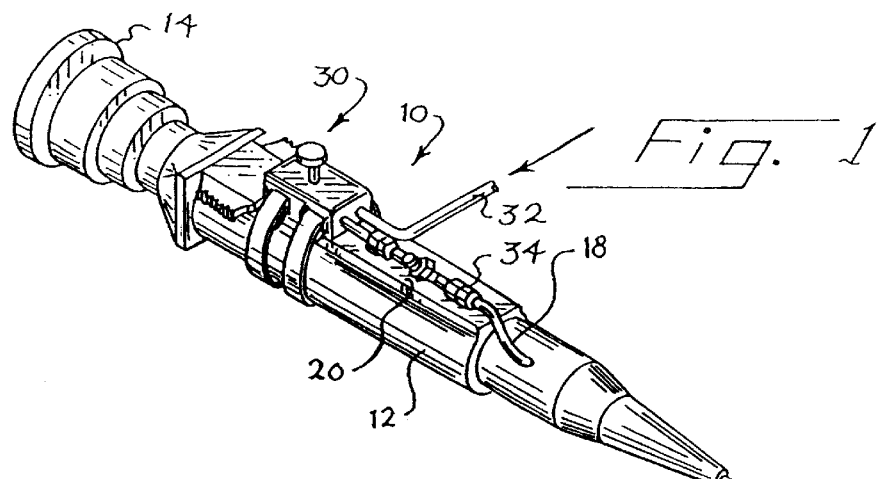
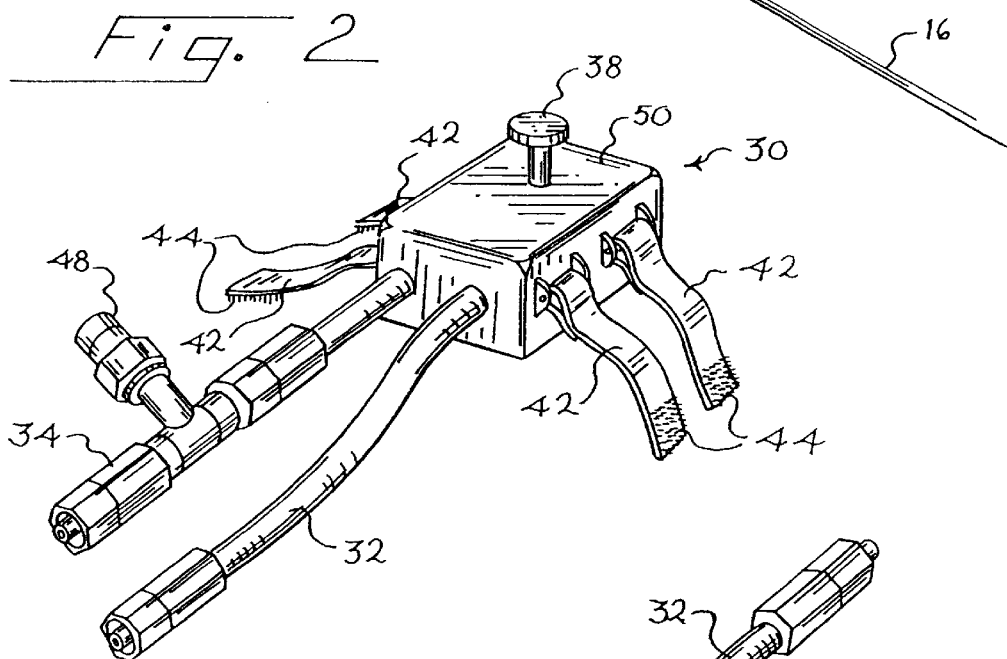
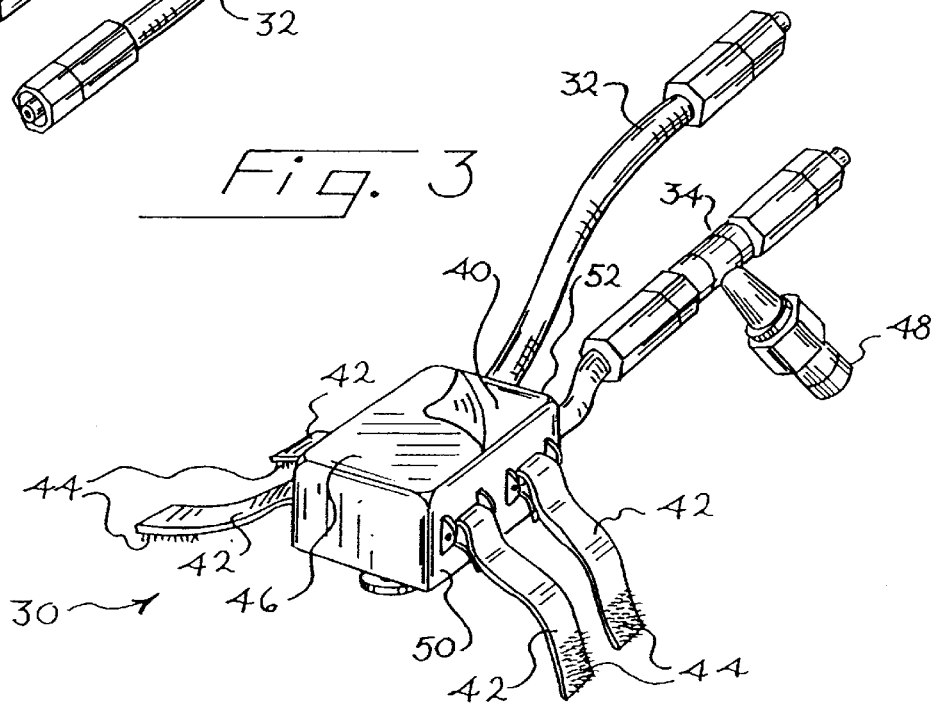

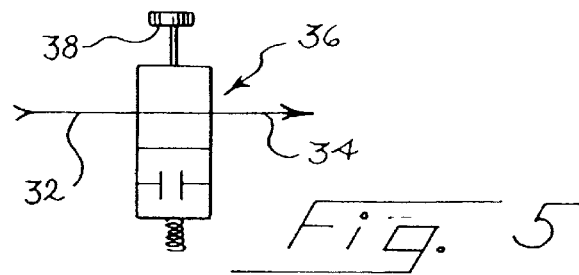
Fig. 5
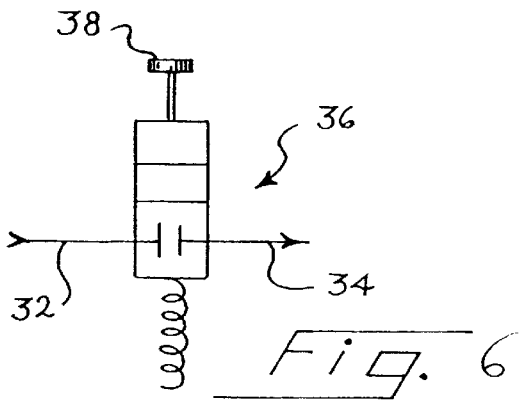
Fig. 6
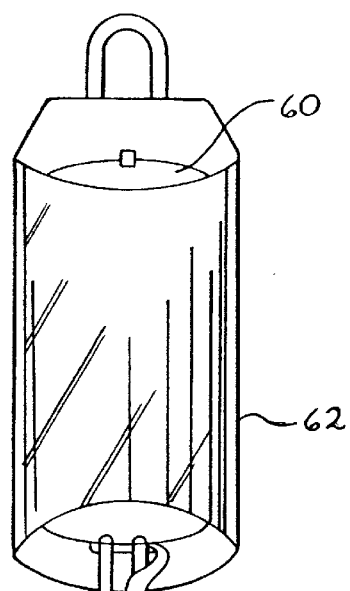
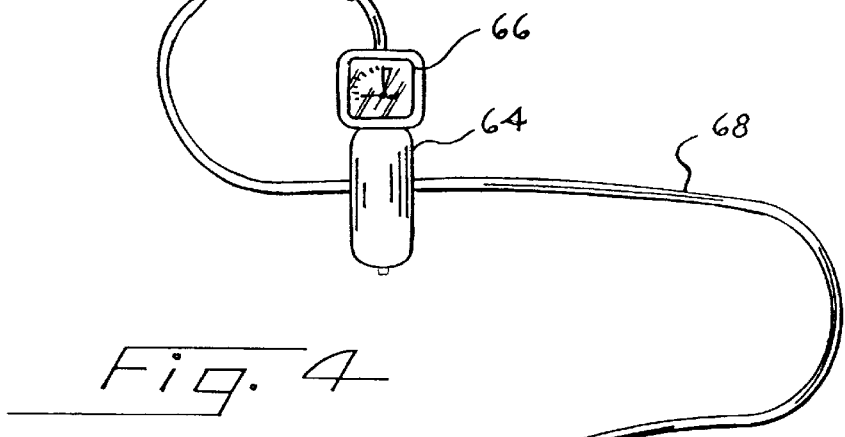
Fig. 4
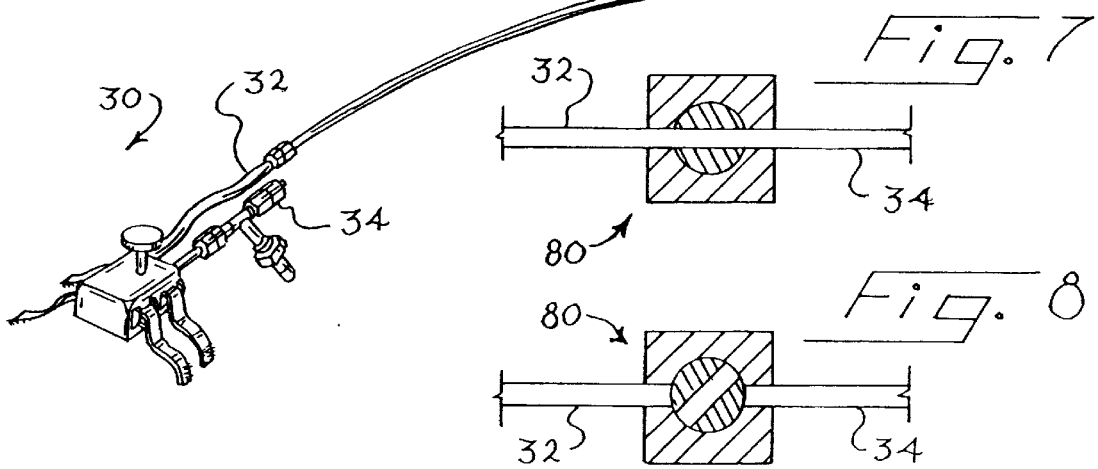
Fig. 7
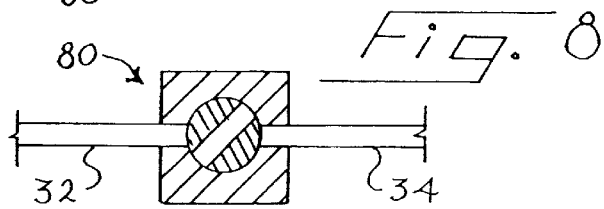
Fig. 8

MODULAR ENDOSCOPE VALVE ASSEMBLY AND METHOD

BACKGROUND

The present invention relates to endoscopic surgical devices, and in particular to valve assemblies used to control the flow of irrigation fluid in such devices.

Endoscopic devices are customarily provided with an irrigation port that conducts an irrigation liquid to the viewing area at the end of the endoscopic device. One prior-art approach is to pressurize irrigation fluid in an IV fluid bag, and then to supply the pressurized irrigation fluid directly into an endoscope such as an ureteroscope. The endoscope includes integral valves that are generally operated with one hand while the other hand holds the handpiece of the endoscope. The advantage of this system is that the irrigation fluid is pressurized, thereby providing dilation of a ureter and good visibility. One potential disadvantage with this type of irrigating system is that it may be difficult to control fluid flow since two hands are required. If the fluid flow is not controlled properly, a stone can be dislodged back into the middle or upper ureter by an excessively high rate of flow. Also, in the event of extravasation, uncontrolled amounts of fluid can flow into the retroperitoneum.

Another type of irrigation system is a hand-operated, pressurized irrigating system commercially manufactured by Bard, Boston Scientific, and ACMI. This approach allows the amount of fluid being injected to be controlled, but the apparatus is relatively bulky. This system is mounted separately from the ureteroscope, and separate hands are used to hold the handpiece of the ureteroscope and to control the flow of irrigation fluid. On occasion, an assistant controls fluid flow while the physician holds the endoscope in the left hand and performs an endoscopic procedure with the right hand. In this case, precise control of the rate of fluid flow is difficult, because oral instructions are slower and less precise than direct manual control by the physician.

A third type of irrigation system includes two or more syringes that are operated by an assistant one at a time to supply pressurized irrigation fluid to the endoscopic device. Generally a valve is provided that allows the assistant to fill one of the syringes while the other is in use.

A fourth type of irrigation system includes a roller pump mechanism that delivers irrigation fluid at a constant set pressure. This system may incorporate a blow-off valve to prevent excessive pressure, and it is generally used in endoscopic specialties such as orthopedics in performing arthroscopies. This system requires the use of an electric motor and controller, and it is therefore costly and bulky.

Goodman U.S. Pat. No. 4,567,880 discloses an endoscopic device having a three-way valve forming a permanent portion of the handpiece of the endoscope. This system allows a physician to control the flow of irrigation fluid with the same hand as that used to hold the handpiece. However, the Goodman system requires a specially constructed endoscope, and the irrigation system is an integral part of the endoscope. This limits the irrigation system to use with one particular endoscope.

The present invention is directed to an improved system and method for controlling the flow of irrigation fluid in an endoscopic device.

SUMMARY

The preferred embodiment described below includes a modular valve assembly having a housing that carries an inlet port, an outlet port and a valve. The valve can be manually controlled by a user with the hand holding the endoscope to selectively allow or block fluid flow from the inlet port to the outlet port.

In use, the housing is releasably mounted to the handpiece of an endoscope by a pressure-sensitive adhesive, strap, or other fastener. The inlet port is connected to a source of pressurized irrigation fluid and the outlet port is connected to the irrigation port of the endoscope. The physician can then use a single hand to perform both the function of holding the handpiece and the function of controlling the flow of irrigation fluid. This leaves the other hand free for performing a surgical procedure via the working port of the endoscope, e.g., positioning and manipulating a stone extraction basket. Once the surgical procedure is completed, the modular housing can simply be removed from the endoscope and discarded. This eliminates the need to clean the valve or the ports of the valve assembly.

This section has been provided by way of general introduction, and it should not be used to narrow the scope of the following claims.

BRIEF DESCRIPTION OF THE DRAWINGS

FIG. 1 is a perspective view of a ureteroscope on which is mounted a modular valve assembly.

FIG. 2 is a top perspective view of the valve assembly of FIG. 1, prior to mounting on the ureteroscope.

FIG. 3 is a bottom perspective view of the valve assembly of FIG. 2.

FIG. 4 is a perspective view of the valve assembly of FIGS. 2 and 3 connected to a source of pressurized irrigation fluid.

FIGS. 5 and 6 are schematic views showing the valve of the valve assembly of FIGS. 1–3 in the opened and closed positions, respectively.

FIGS. 7 and 8 are schematic views of an alternative, rotary-motion valve in the opened and closed positions, respectively.

DETAILED DESCRIPTION OF THE PRESENTLY PREFERRED EMBODIMENTS

Figure 9:
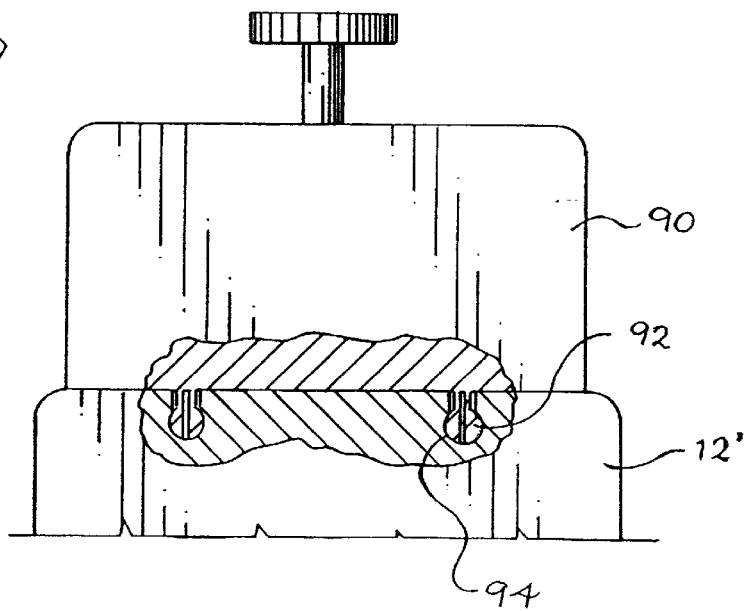
FIG. 9 is a fragmentary sectional view of another modular valve assembly of this invention mounted on a ureteroscope.

Turning now to the drawings, FIG. 1 is a perspective view of an endoscopic device 10 that in this embodiment is a ureteroscope. The ureteroscope 10 includes a handpiece 12 that carries an eyepiece 14 at one end and a shaft 16 at the other end. An irrigation port 18 is carried by the handpiece 12, and irrigation fluid introduced via the irrigation port 18 is conducted to the viewing area at the end of the shaft 16 that is inserted into the patient. The handpiece 12 also defines an exterior surface 20.

The endoscopic device 10 can take any suitable form, and the present invention is not limited to any particular embodiment. For example, the endoscopes of any of the following U.S. Patents can be adapted for use with this invention: Wallace U.S. Pat. No. 2,691,370, Ibe U.S. Pat. No. 4,132,227, Goodman U.S. Pat. No. 4,567,880, Cho U.S. Pat. No. 5,083,549, Muller U.S. Pat. No. 5,199,417, Bonati U.S. Pat. No. 5,290,279, and Odanacka U.S. Pat. No. 5,830,126.

Conventional endoscopes such as the ureteroscopes manufactured by ACMI, Wolf, Olympus and Storz are also well-adapted for use with this invention. This list is intended only by way of illustration, in the widest variety of ureteroscopes, arthroscopes, and laparoscopes can be used with this invention, including flexible, semi-rigid, and rigid endoscopes.

In use, the physician holds the handpiece with one hand, thereby presenting the eyepiece for viewing and positioning the shaft as desired. The other hand is typically used to manipulate surgical tools introduced into the patient via the working port on the shaft. As shown in FIG. 1, a modular endoscope valve assembly 30 is releasably secured to the handpiece 12. This valve assembly 30 is shown in greater detail in FIGS. 2 and 3, and it includes an inlet port 32 and an outlet port 34. In use the inlet port 32 is releasably connected to a source of pressurized irrigation fluid, and the outlet port 34 is releasably connected to the irrigation port 18 of the handpiece.

The valve assembly 30 includes a valve that is interposed between the inlet port 32 and the outlet port 34 and is controlled by a valve actuator 38. The valve assembly 30 also includes a housing 50 that includes a mounting surface 52. The mounting surface 52 carries a pressure-sensitive adhesive 40 initially covered by a release paper 46. The housing 50 also supports a pair of straps 42 that include respective hook-and-loop fasteners 44. A contrast-introduction port 48 is provided in fluid communication with the outlet port 34.

FIG. 4 shows the manner in which the inlet port 32 of the valve assembly 30 can be releasably connect to a source of pressurized irrigation fluid, in this case contained within an IV bag 60. The IV bag 60 is disposed within a pressure cuff 62 that can be inflated with an inflator 64 to a pressure indicated by a pressure gauge 66. Standard Luer-lock fittings can be used to connect the inlet port 32 to a tube 68 that is in turn connected to the IV bag 60. The IV bag contains a conventional irrigation fluid, which is pressurized by inflating the pressure cuff 62 to a desired pressure with the inflator 64.

FIGS. 5 and 6 show two schematic views of the valve 36 of the valve assembly 30. In FIG. 5 the valve actuator 38 is depressed and the valve 36 allows fluid flow from the inlet port 32 to the outlet port 34. When manual pressure is removed from the valve actuator 38, the valve 36 returns to the position of FIG. 6, in which the valve 36 blocks the flow of fluid between the inlet and the outlet ports 32, 34. Alternatively, the valve 38 may be arranged such that fluid flow is blocked when the actuator 38 is depressed and unblocked when the actuator 38 is released.

The valve 36 of FIGS. 5 and 6 is a linear valve that slides along a linear axis between the opened position of FIG. 5 and the closed position of FIG. 6. Other types of valves are suitable, including the linear valve of U.S. Pat. No. 4,238,108 and the rotary valve 80 of FIGS. 7 and 8. A rotary valve 80 rotates about an axis between the opened position of FIG. 7 and the closed position of FIG. 8, and the associated valve actuator (not shown in FIGS. 7 and 8) moves in a rotary motion as well.

In use, the valve assembly 30 is distributed separately from the endoscope 10. In this embodiment, the valve assembly 30 is shaped to fit on a wide variety of endscopes 10 such that the endoscope 10 does not have to be specially shaped or configured for the valve assembly 30. Prior to an endoscopic procedure, the release paper 46 is removed, thereby exposing the pressure-sensitive adhesive 40 on the mounting surface 52. Then the valve assembly 30 is placed on the exterior surface 20 of the endoscope 10, and the pressure-sensitive adhesive 40 releasably holds the valve assembly 30 in place. The straps 42 are positioned around the handpiece 12, and the hook-and-loop fasteners 44 are secured together to hold the valve assembly 30 in place.

Either before or after the valve assembly 30 is secured to the handpiece 12, the inlet port 32 is releasably secured to the tube 68 (FIG. 4) and the outlet port 34 is releasably secured to the irrigation port 18 of the handpiece 12 (FIG. 1). Preferably, the valve assembly 30 is flushed after it is connected to the tube 68 and before it is connected to the irrigation port 18.

The physician then performs the desired endoscopic procedure, using a single hand both to hold the handpiece 12 and to control the flow of pressurized irrigation fluid with the valve assembly 30. A part of the hand that holds the handpiece (e.g. the fingers or the heel) is used to move the valve actuator.

Once the endoscopic procedure has been completed, the valve assembly 30 can simply be removed from the endoscope 10 by releasing the hook-and-loop fasteners 44 and lifting or twisting the valve assembly 10 away from the handpiece 12 until the pressure-sensitive adhesive 40 releases.

The valve assembly 30 described above uses both a pressure-sensitive adhesive and a set of straps to releasably secure the valve assembly 30 in place on the handpiece 12. In alternative embodiments the adhesive may be used without the reinforcing straps, or the reinforcing straps can be used without the adhesive. Also, other types of fasteners can be used to releasably hold the valve assembly in place on the endoscope.

FIG. 9 shows a second preferred embodiment 90 of the modular valve assembly of this invention. The valve assembly 90 is identical to the valve assembly 30 described above except for the manner of releasably attaching the valve assembly 90 to the handpiece 12'. In this case the valve assembly 90 is provided with mechanical fasteners 92 and the handpiece 12' is provided with mating mechanical fasteners 94 such that the valve assembly 90 can be snapped in place on the handpiece 12' and removed from the handpiece 12' as desired. In this example, the fasteners 92 take the form of protruding studs and the mating fasteners 94 take the form of recesses shaped to receive the fasteners 92 in a snap-lock action.

Figure 10:
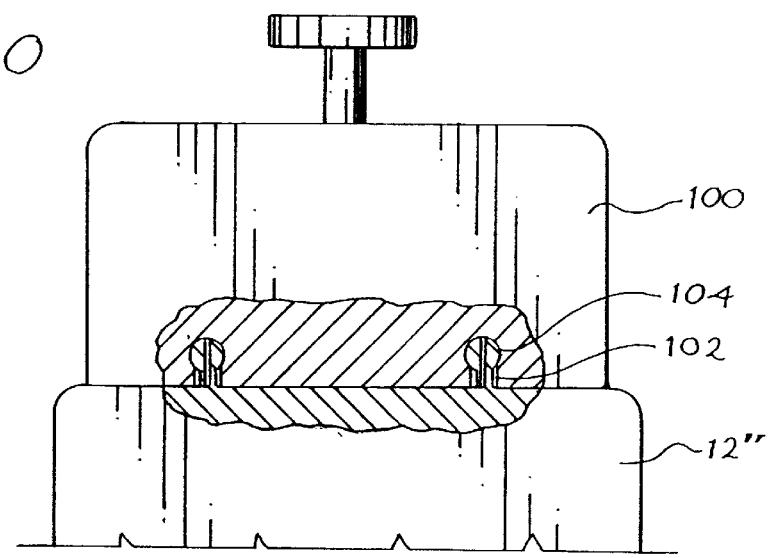
FIG. 10 is a fragmentary sectional view of yet another modular valve assembly of this invention.

FIG. 10 shows portions of a third valve assembly 100 which is similar to that of FIG. 9 except that the fasteners 102 are shaped as recesses and the mating fasteners 104 are shaped as protruding studs that fit into the fasteners 102 in a snap-lock manner.

Figure 11:
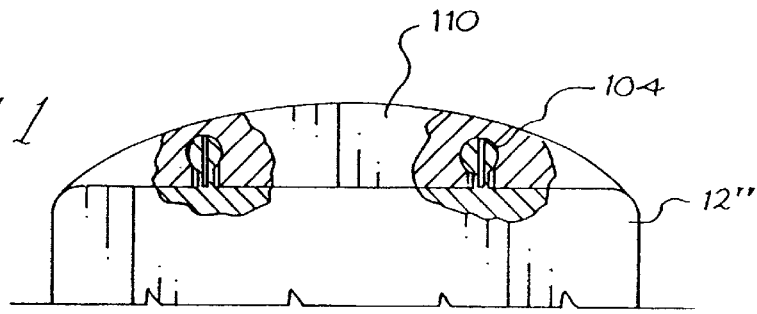
FIG. 11 is a fragmentary sectional view of the ureteroscope of FIG. 10 and a cover plate.

FIG. 11 shows the handpiece 12" of FIG. 10 with a cover 110 snapped in place on the mating fasteners 104. The cover 110 covers the mating fasteners 104 when a valve assembly is not in place on the handpiece 12".

It should be apparent from the foregoing description that the improved modular valve assembly of this invention provides the important advantage that little or no modification is required to a conventional endoscope, yet the physician using the endoscope is provided with improved control over the flow of irrigation fluid. In particular, the physician can use direct finger pressure to modulate the flow of irrigation fluid as desired, while still leaving one hand free for surgical procedures. In this way, the need for a trained surgical nurse is reduced, and the physician's control over irrigation fluid flow is improved. The valve assembly described above is well suited for use with a wide variety of endoscopes including modern, small endoscopes that are too small for built-in valves.

Of course, it should be understood that a wide range of changes and modifications can be made to the preferred embodiments described above. For example, the valve of the valve assembly can take any suitable form, and it is not limited to the specific examples described above. The motion used to open or close the valve 36 can be varied as appropriate for the application, and it can include a lifting motion, a depressing motion, a sliding motion parallel to the length of the handpiece, or a rotating motion as desired. As a further alternative, the valve may be implemented as an element that pinches a resilient tube to slow or block flow through the tube. Thus, the valve can be implemented as a one-piece or a multiple-piece system having sliding, hinged, rotating or other motions.

Similarly, the mechanical fasteners that releasably hold the valve assembly in place on the handpiece of the endoscope can take any suitable form, and such fasteners are not limited to the adhesives, straps, snap-lock studs, and recesses described above. Many other mechanical fasteners can be adapted for use with this invention, as for example linear or rotary guides (including, e.g., dovetail guides or bayonet sockets) and various types of resilient or bendable elements that releasably hold the valve assembly in place.

As used herein, the term "position" is intended broadly to encompass a range of positions. Thus, the valve may block fluid flow between the inlet and outlet ports in a range of blocking positions and the valve may allow fluid to flow from the inlet port to the outlet port in a range of opened positions. The valve may be configured as an on/off valve or as a modulating valve.

The term "handpiece" is intended broadly to refer to the part of an endoscope that carries the eyepiece and is held by the user, whether referred to as the handpiece, the bridge, or by some other term by the manufacturer of the endoscope.

Also, any suitable structure can be used for pressurizing the irrigation liquid, including simple gravity feeds in some examples.

The foregoing detailed description has discussed only a few of the many forms that this invention can take. This detailed description is therefore intended by way of illustration and not by way of limitation. It is only the following claims, including all equivalents, that are intended to define the scope of this invention.

What is claimed is:

1. A medical endoscope with a releasably mounted modular endoscope valve assembly comprising:
    a medical endoscope comprising a handpiece that carries an eyepiece, the handpiece comprising an exterior surface and an irrigation port; and
    a modular endoscope valve assembly releasably mounted to the exterior surface of the endoscope, the modular endoscope valve assembly comprising:
        a housing comprising an inlet port, an outlet port, and a mounting surface, wherein the outlet port is releasably connected to the irrigation port of the endoscope;
        a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and
        a pressure-sensitive adhesive carried by the mounting surface, wherein the mounting surface of the housing is releasably held in place on the exterior surface by the adhesive.

2. The invention of claim 1 wherein the endoscope comprises a uteroscope.

3. A medical endoscope with a releasably mounted modular endoscope valve assembly comprising:
    a medical endoscope comprising a handpiece that carries an eyepiece, the handpiece comprising an exterior surface and an irrigation port; and
    a modular endoscope valve assembly releasably mounted to the exterior surface of the endoscope, the modular endoscope valve assembly comprising:
        a housing comprising an inlet port, an outlet port, and a mounting surface, wherein the outlet port is releasably connected to the irrigation port of the endoscope;
        a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and
        a strap carried by the housing, wherein the mounting surface of the housing is releasably held in place on the exterior surface by the strap.

4. The invention of claim 3 wherein the endoscope comprises a ureteroscope.

5. A medical endoscope with a releasably mounted modular endoscope valve assembly comprising:
    a medical endoscope comprising a handpiece that carries an eyepiece, the handpiece comprising an exterior surface and an irrigation port; and
    a modular endoscope valve assembly releasably mounted to the exterior surface of the endoscope, the modular endoscope valve assembly comprising:
        a housing comprising an inlet port, an outlet port, and a mounting surface, wherein the outlet port is releasably connected to the irrigation port of the endoscope;
        a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and
        a mechanical fastener carried by the mounting surface, the mechanical fastener releasably engaged with a mating fastener on the handpiece of the endoscope.

6. The invention of claim 1, or 5 further comprising a strap carried by the housing and operative to releasably secure the housing to the handpiece of the endoscope.

7. The invention of claim 1 or 5 wherein the actuator is mounted to slide linearly between the first and second positions.

8. The invention of claim 1, 3 or 5 wherein the actuator is mounted to rotate between the first and second positions.

9. The invention of claim 5 wherein the endoscope comprises a uteroscope.

10. The invention of claim 1, 3 or 5 wherein the outlet port comprises a contrast-introduction port.

11. A method for enhancing control efficiency of a medical endoscope, the method comprising:
    (a) providing a medical endoscope comprising a handpiece that carries an eyepiece, the handpiece comprising an exterior surface and an irrigation port;
    (b) providing a modular endoscope valve assembly comprising:

a housing comprising an inlet port, an outlet port, and a mounting surface;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;

a pressure-sensitive adhesive carried by the mounting surface;

(c) releasably securing the valve assembly to the exterior surface of the handpiece with the adhesive;

(d) removably coupling the outlet port of the valve assembly to the irrigation port of the handpiece; and then (e) removing the valve assembly from the exterior surface of the handpiece after a surgical procedure.

12. The method of claim 11 wherein the valve assembly of (b) further comprises a strap carried by the housing.

13. The method of claim 12 further comprising:

(f) releasably securing the valve assembly to the handpiece with the strap after (c) and before (e).

14. A method for enhancing control efficiency of a medical endoscope, the method comprising:

(a) providing a medical endoscope comprising a handpiece that carries an eyepiece, the handpiece comprising an exterior surface and an irrigation port;

(b) providing a modular endoscope valve assembly comprising:

a housing comprising an inlet port, an outlet port, and a mounting surface;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;

a strap carried by the housing;

(c) releasably securing the valve assembly to the exterior surface of the handpiece with the strap;

(d) removably coupling the outlet port of the valve assembly to the irrigation port of the handpiece; and then (e) removing the valve assembly from the exterior surface of the handpiece after a surgical procedure.

15. A method for enhancing control efficiency of a medical endoscope, the method comprising:

(a) providing a medical endoscope comprising a handpiece that carries an eyepiece, the handpiece comprising an exterior surface and an irrigation port;

(b) providing a modular endoscope valve assembly comprising:

a housing comprising an inlet port, an outlet port, and a mounting surface;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;

(c) releasably securing the valve assembly to the exterior surface of the handpiece;

(d) removably coupling the outlet port of the valve assembly to the irrigation port of the handpiece; and then (e) removing the valve assembly from the exterior surface of the handpiece after a surgical procedure.

16. A medical endoscope with a releasably mounted modular endoscope valve assembly comprising:

a medical endoscope comprising an exterior surface and an irrigation port; and a modular endoscope valve assembly releasably mounted to the exterior surface of the endoscope, the modular endoscope valve assembly comprising:

a housing comprising an inlet port, an outlet port, and a mounting surface, wherein the outlet port is releasably connected to the irrigation port of the endoscope;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and a pressure-sensitive adhesive carried by the mounting surface, wherein the mounting surface of the housing is releasably held in place on the exterior surface by the adhesive.

17. The invention of claim 16 wherein the endoscope comprises a uteroscope.

18. A medical endoscope with a releasably mounted modular endoscope valve assembly comprising:

a medical endoscope comprising an exterior surface and an irrigation port; and a modular endoscope valve assembly releasably mounted to the exterior surface of the endoscope, the modular endoscope valve assembly comprising:

a housing comprising an inlet port, an outlet port, and a mounting surface, wherein the outlet port is releasably connected to the irrigation port of the endoscope;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and a strap carried by the housing, wherein the mounting surface of the housing is releasably held in place on the exterior surface by the strap.

19. The invention of claim 18 wherein the endoscope comprises a uteroscope.

20. A medical endoscope with a releasably mounted modular endoscope valve assembly comprising:

a medical endoscope comprising an exterior surface and an irrigation port; and a modular endoscope valve assembly releasably mounted to the exterior surface of the endoscope, the modular endoscope valve assembly comprising:

a housing comprising an inlet port, an outlet port, and a mounting surface, wherein the outlet port is releasably connected to the irrigation port of the endoscope;

a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and a mechanical fastener carried by the mounting surface, the mechanical fastener releasably engaged with a mating fastener on the endoscope.

21. The invention of claim 16 or 20 further comprising a strap carried by the housing and operative to releasably secure the housing to the endoscope.

22. The invention of claim 16, 18 or 20 wherein the actuator is mounted to slide linearly between the first and second positions.

23. The invention of claim 16, 18 or 20 wherein the actuator is mounted to rotate between the first and second positions.

24. The invention of claim 20 wherein the endoscope comprises a ureteroscope.

25. The invention of claim 16, 18 or 20 wherein the outlet port comprises a contrast-introduction port.

26. A method for enhancing control efficiency of a medical endoscope, the method comprising:
   (a) providing a medical endoscope comprising an exterior surface and an irrigation port;
   (b) providing a modular endoscope valve assembly comprising:
      a housing comprising an inlet port, an outlet port, and a mounting surface;
      a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;
      a pressure-sensitive adhesive carried by the mounting surface;
   (c) releasably securing the valve assembly to the exterior surface of the endoscope with the adhesive;
   (d) removably coupling the outlet port of the valve assembly to the irrigation port of the endoscope; and then
   (e) removing the valve assembly from the exterior surface of the endoscope after a surgical procedure.

27. The method of claim 26 wherein the valve assembly of (b) further comprises a strap carried by the housing.

28. The method of claim 27 further comprising:
   (f) releasably securing the valve assembly to the endoscope with the strap after (c) and before (e).

29. A method for enhancing control efficiency of a medical endoscope, the method comprising:
   (a) providing a medical endoscope comprising an exterior surface and an irrigation port;
   (b) providing a modular endoscope valve assembly comprising:
      a housing comprising an inlet port, an outlet port, and a mounting surface;
      a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;
      a strap carried by the housing;
   (c) releasably securing the valve assembly to the exterior surface of the endoscope with the strap;
   (d) removably coupling the outlet port of the valve assembly to the irrigation port of the endoscope; and then
   (e) removing the valve assembly from the exterior surface of the endoscope after a surgical procedure.

30. A method for enhancing control efficiency of a medical endoscope, the method comprising:
   (a) providing a medical endoscope comprising an exterior surface and an irrigation port;
   (b) providing a modular endoscope valve assembly comprising:
      a housing comprising an inlet port, an outlet port, and a mounting surface;
      a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port;
   (c) releasably securing the valve assembly to the exterior surface of the endoscope;
   (d) removably coupling the outlet port of the valve assembly to the irrigation port of the endoscope; and then
   (e) removing the valve assembly from the exterior surface of the endoscope after a surgical procedure.

31. The invention of claim 30, wherein the modular endoscope valve assembly comprises a pressure-sensitive adhesive carried by the mounting surface, and wherein (c) comprises releasably securing the valve assembly to the exterior surface of the endoscope with the adhesive.

32. The invention of claim 30, wherein the modular endoscope valve assembly comprises a strap carried by the housing, and wherein (c) comprises releasably securing the valve assembly to the exterior surface of the endoscope with the strap.

33. The invention of claim 30, wherein the modular endoscope valve assembly comprises a mechanical fastener carried by the housing, wherein the endoscope comprises a mating fastener, and wherein (c) comprises releasably engaging the mechanical fastener with the mating fastener.

34. The invention of claim 30, wherein the modular endoscope valve assembly comprises a resilient element carried by the housing, and wherein (c) comprises releasably securing the valve assembly to the exterior surface of the endoscope with the resilient element.

35. A modular endoscope valve assembly comprising:
   a housing comprising an inlet port, an outlet port, and a mounting surface shaped to mount on at least three locations on an endoscope;
   a valve carried by the housing and coupled between the inlet port and the outlet port, the valve comprising a manually-controlled actuator movable by a user between a first position, in which the valve blocks flow from the inlet port to the outlet port, and a second position, in which the valve allows flow from the inlet port to the outlet port; and
   a resilient element coupled with the housing and operative to releasably secure the housing to the endoscope.

36. The invention of claim 35 further comprising a pressure-sensitive adhesive carried by the mounting surface and operative to releasably secure the housing to the endoscope.

37. The invention of claim 35 further comprising a strap carried by the housing and operative to releasably secure the housing to the endoscope.

38. The invention of claim 35, wherein the endoscope comprises a ureteroscope.

* * * * *

UNITED STATES PATENT AND TRADEMARK OFFICE
CERTIFICATE OF CORRECTION

PATENT NO. : 6,533,720 B1
DATED : March 18, 2003
INVENTOR(S) : Avtar S. Dhindsa

It is certified that error appears in the above-identified patent and that said Letters Patent is hereby corrected as shown below:

Column 6,
Line 52, delete "1 or 5" and substitute -- 1, 3 or 5 -- in its place.

Signed and Sealed this

Fifth Day of October, 2004

JON W. DUDAS
*Director of the United States Patent and Trademark Office*